US011390853B2

(12) United States Patent
Pokorski et al.

(10) Patent No.: US 11,390,853 B2
(45) Date of Patent: Jul. 19, 2022

(54) FREEZE DRIED VIRAL NANOPARTICLE CONSTRUCTS

(71) Applicant: CASE WESTERN RESERVE UNIVERSITY, Cleveland, OH (US)

(72) Inventors: Jonathan Pokorski, San Diego, CA (US); Nicole Steinmetz, San Diego, CA (US); Parker Lee, Los Angeles, CA (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 63 days.

(21) Appl. No.: 16/859,400

(22) Filed: Apr. 27, 2020

(65) Prior Publication Data

US 2020/0339961 A1 Oct. 29, 2020

Related U.S. Application Data

(60) Provisional application No. 62/839,438, filed on Apr. 26, 2019.

(51) Int. Cl.
*C12N 7/00* (2006.01)

(52) U.S. Cl.
CPC ...... *C12N 7/00* (2013.01); *C12N 2770/18023* (2013.01); *C12N 2770/18051* (2013.01); *C12N 2770/32023* (2013.01); *C12N 2770/32051* (2013.01); *C12Y 301/27005* (2013.01)

(58) Field of Classification Search
None
See application file for complete search history.

(56) References Cited

U.S. PATENT DOCUMENTS

| | | | |
|---|---|---|---|
| 5,004,606 | A | 4/1991 | Frincke |
| 6,884,422 | B1 | 4/2005 | Liu et al. |
| 9,399,059 | B2 | 7/2016 | Morrison |
| 2005/0019270 | A1 | 1/2005 | Finlay et al. |
| 2007/0258889 | A1 | 11/2007 | Douglas |
| 2007/0284545 | A1 | 12/2007 | Isacsson et al. |
| 2018/0265552 | A1* | 9/2018 | Belval .................. C07K 14/005 |

FOREIGN PATENT DOCUMENTS

| | | |
|---|---|---|
| JP | 2009524699 A | 7/2009 |
| WO | 01/18199 A1 | 3/2001 |
| WO | 2001/026682 A2 | 4/2001 |
| WO | 2003092623 A2 | 11/2003 |
| WO | 2012078069 A1 | 6/2012 |
| WO | 2013181557 A1 | 12/2013 |
| WO | 2015/039255 A1 | 3/2015 |
| WO | 2016/073972 A1 | 5/2016 |

OTHER PUBLICATIONS

Yordanova et al. (2005) Prediction of the Preservation of Lyophilized Tobamoviruses, Biotechnology & Biotechnological Equipment, 19:sup1, 46-51.*
Zheng et al. Freeze-Drying to Produce Efficacious CPMV Virus-like Particles. Nano Lett. 2019, 19, 2099-2105.*
Storni et al. Nonmethylated CG Motifs Packaged into Virus-Like Particles Induce Protective Cytotoxic T Cell Responses in the Absence of Systemic Side Effects. The Journal of Immunology, 2004, 172: 1777-1785.*
Sainsbury et al. Genetic engineering and characterization of Cowpea mosaic virus empty virus-like particles. Methods Mol Biol. 2014;1108:139-53.*
Office action for Japanese Patent Application No. 2017-524349, dated Jan. 31, 2020.
Miermont et al., "Cowpea Mosaic Virus Capsid: A promising Carrier for the Development of Carbohydrate Based Antitumor Vaccines", Chem. Eur. J., 2008, vol. 14, pp. 4939-4947.
Sheen et al., "Stimulating Antitumor Immunity with Nanoparticles", Wiley Interdiscip Rev Nanomed Nanobiotechnol, Oct. 2014, vol. 6, pp. 496-505.
Office action for Chinese Patent Application No. 201580063662.6, dated Mar. 4, 2020.
Office action for European Patent Application No. 15 857 504.3-1111, dated Mar. 18, 2020.
Yildiz et al., "Applications of viral nanoparticles in medicine", Current Opinion in Biotechnology, vol. 22, Issue 6, pp. 901-908.
Aljabali, et al., "CPMV-DOX Delivers", Molecular Pharmaceutics, 2013, 10, pp. 3-10.
Wen, et al., "Interior Engineering of a Viral Nanoparticle and its Tumor Homing Properties" Macromolecules, vol. 13, No. 12, Dec. 2012.
Agrawal, et al., "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012.
Brennan, et al., "Cowpea Mosaic Virus as a Vaccine Carrier of Heterologous Antigens", Molecular Biotechnology, vol. 17, No. 1, Jan. 2001.
Gonzalez, et al., "Interaction of Cowpea Mosaic Virus (CPMV) Nanoparticles with Antigen Presenting Cells in Vitro and In Vivo", PLOS ONE, vol. 4, No. 11, Nov. 2009.
Iizotte, et al., "Plant-derived viral-like nanoparticle immunotherapy suppress development of metastatic lung cancer", Journal of Immunology, vol. 194, Issue 1 Supplement, May 2015.
Patrick H. Lizotte, "Novel approaches to targeting innate immunity for cancer immunotherapy", Proquest Dissertations Publishing, May 2015.
European Search Report for Patent Application No. 15857504.3-1111/3215520, dated May 7, 2018.
Supplementary European Search Report for Patent Application No. 15857504.3-1111/3215520, dated May 28, 2018.
International Search Report for Application No. PCT/US15/59675.
Plchova et al. Expression of Human papillomavirus 16 E7ggg oncoprotein on N- and C-terminus of Potato virus X coat protein in bacterial and plant cells. Protein Expression and Purification 77 (2011) 146-152.
Smyth etal. Treatment of rapidly growing K-BALB and CT26 mouse tumours using Semliki Forest virus and its derived vector. Gene Therapy (2005) 12, 147-159.
Applicant: Case Western Reserve University; "Cancer Immunotherapy Using Virus Particles"; European Patent Application No. 18764856.3 for Supplementary European Search Report dated Dec. 22, 2020; 8 pgs.
Lee, K. L., et al.; "Combination of Plant Virus Nanoparticle-Based in Situ Vaccination with Chemotherapy Potentiates Antitumor Response". Nano letters, 17(7); Epub Jun. 26, 2017; 4019-4028. https://doi.org/10.1021/acs.nanolett.7b00107.

(Continued)

*Primary Examiner* — Nianxiang Zou
(74) *Attorney, Agent, or Firm* — Tarolli, Sundheim, Covell & Tummino LLP (57) ABSTRACT

A method of producing plant virus-like particles includes freeze drying an aqueous solution of plant virus particles to produce a substantially RNA-free plant virus-like particles.

21 Claims, 6 Drawing Sheets

(56) References Cited

OTHER PUBLICATIONS

Nicole F.Steinmetz; "Viral Nanoparticle Multimers"; U.S. Appl. No. 14/761,444, filed Jul. 16, 2015; Final Office Action dated Mar. 11, 2021; 11 pgs.

Nicole F.Steinmetz, et al.; "Coated Plant Virus Imaging Agents"; U.S. Appl. No. 16/279,482, filed Feb. 19, 2019; Non-Final Rejection dated Mar. 23, 2021; 91 pgs.

Inventor: Nicole Steinmetz, "Rod-Shaped Plant Virus Nanoparticles as Imaging Agent Platforms"; U.S. Appl. No. 16/149,828, filed Oct. 2, 2018, Office Action dated Aug. 28, 2020, 22 pgs.

Applicant: Case Western Reserve University; "Cancer Immunotherapy Using Virus Particles"; Office Action, dated Aug. 4, 2020; 3 pgs.

Applicant: Case Western Reserve University; "Plant Virus Particles for Delivery of Antimitotic Agents"; Extended European Search Report; dated Aug. 17, 2020; 11 pgs.

Canan Uluog, et al.: "Intermediate dose of methotrexate toxicity in non-Hodgkin lymphoma", General Pharmacology, vol. 32, 1999, pp. 215-218, XP55711259.

Trevor W. E. Robinson, et al., "The Journal of Investigative Dermatology the Effect of Methotrexate on Cell Division in the Epidermis of the Young Rat"; The Journal of investigative Dermatology, vol. 53, 1969, pp. 223-227, XP55711263.

Jantipa Jobsri, et al.: Plant Virus Particles Carrying Tumour Antigen Activate TLR7 and Induce High Levels of Protective Antibody, Plos One, vol. 10, No. 2, Jan. 1, 2015, pp. 1-16, XP055347065, DOI: 10.1371/journal.pone.0118096.

Pfizer Ltd.: "Package leaflet: Information for the patient", Jan. 1, 2014, XP55565400, Walton Oaks, Tadworth, Surrey, UK Retrieved from the Internet: URL:https://www.medicines.org.uk/emc/files/pil.6184.pdf [retrieved on Mar. 6, 2019].

Alaa A. Al. Aljabali, et al.; "CPMV-DOX Delivers", Molecular Pharmaceutics, vol. 10, No. 1, Jan. 7, 2013, pp. 3-10, XP055347068, US ISSN: 1543-8384, DOI: 10.1021/MP3002057.

Sourabh Shukla, et al.: "The Impact of Aspect Ratio on the Biodistribution and Tumor Homing of Rigid Soft-Matter Nanorods", Advanced Healthcare Materials, vol. 4, No. 6, Apr. 1, 2015, pp. 874-882, XP055473103, DE ISSN: 2192-2640, DOI: 10.1002/adhm.201400641.

Francisco, Joseph A., et al.; "cAC10-vcMMAE, an anti-CD30-monomethyl auristatin E conjugate with potent and selective anti-tumor activity", Blood, American Society of Hematology, US, vol. 102, No. 4, Aug. 15, 2003, pp. 1458-1465, XP002738948, ISSN: 0006-4971, DOI: 10.1182/BLOOD-2003-01-0039.

TMV structures on the Research Collaboratory for Structural Bioinformatics (RCSB) Protein Data Bank (PDB) website, www.rcsb.org, such as entries 3J06 and 2XEA.

Hesketh, Emma, L., et al., "The Structures of a naturally empty cowpea mosaic virus particle and its genome-containing counterpart by cyro-electron microscopy", Sci. Rep., 7:539, 2017.

Hu, He, et al., "Development of a Virus-Like Particle-Based Anti-HER2 Breast Cancer Vaccine", Cancers 2021, 13, 2909.

Klug, A., "The Tobacco Mosaic Virus particle: structure and assembly" Phil. Trans. R. Soc. Lond. B (1999) 354-531-535.

Hu, He, et al., "Development of a Virus-Like Particle-Based Anti-HER2 Breast Cancer Vaccine", Cancers 2021, 13, 2909. Supplemental Materials.

\* cited by examiner

Wild-type CPMV

Fig. 4A

Lyo-eCPMV

Fig. 4B

Lyo-eCPMV

Fig. 5A eCPMV

FREEZE DRIED VIRAL NANOPARTICLE CONSTRUCTS

RELATED APPLICATION

This application claims priority from U.S. Provisional Application No. 62/839,438, filed Apr. 26, 2019, the subject matter of which is incorporated herein by reference in its entirety.

GOVERNMENT FUNDING

This invention was made with government support under Grant No. R21EB024874, awarded by the National Institutes of Health. The United States government has certain rights in the invention.

BACKGROUND

Viral nanoparticles (VNPs) are an emerging class of nanomaterials and have broad applications in materials science, agriculture, energy and medicine. The appeal of such particles is due to their near monodispersity, wide variety of shapes and sizes, and precise placement of functional groups for chemical or genetic modification. The use of VNPs as platforms for immunoengineering is of particular interest, since their size generally lies between 20 and 300 nm offering effective recognition by dendritic cells (DCs) or other antigen-presenting cells (APC). In addition, the placement of epitopes occurs in a regular and repeating pattern about the capsid thus activating the pathogen-associated molecular pattern (PAMP) response of the innate immune system.

Virus-like particles (VLPs) are a subclass of VNPs lacking genomic material but retaining capsid structure and thus can elicit a similar immune response. The absence of nucleic acids makes them non-infectious and eliminates a potential uncontrolled immunostimulatory source, rendering VLPs ideal building blocks for immunotherapy. As such, several VLP vaccines are in clinical trials or have been approved by the FDA. The most well-known is that of Gardasil, consisting of the major capsid protein of several human papilloma virus (HPV) subtypes. VLPs have also been approved and are commonly used for vaccination against Hepatitis B and Hepatitis E. Beyond this, a vast amount of resources has been dedicated toward pre-clinical and clinical trials of VLP vaccine candidates. These novel therapies can be directed against the VLP itself or against antigens decorated about the VLP surface.

One of the most sought-after areas in vaccine development is the development of cancer immunotherapies. A recent exciting innovation in cancer immunotherapy is the generation of in situ cancer vaccines, where an immunostimulatory agent is directly administered to a tumor site. The attributes of this class of therapy are that they are near universal immunotherapies, since no antigen is displayed. It elicits a strong memory anti-tumor immune response by inducing immunogenic cancer cell death, facilitating the release of tumor-associated antigens and enhancing the activation and increasing the number of APCs to induce anti-tumor T cell responses, resulting in systemic anti-tumor immunity. One of the tools used for in situ vaccination are oncolytic viruses, though the degree of immune responses they induce can relate to the particular virus used, the tumor burden, and the immunogenicity. What's more, the safety concerns like infection and proliferation of oncolytic viruses cannot be eliminated since they are infectious.

Recently, plant viruses emerged as in situ vaccines, and showed exciting therapeutic effects in curing metastatic disease. In one example, papaya mosaic virus has the capacity to activate the innate immune system and reduce tumor volume in a melanoma murine model. Furthermore, VLPs derived from cowpea mosaic virus engineered to lack the viral RNA (eCPMV) achieve therapeutic activity in various poorly immunogenic murine tumor models, induce long-lasting antitumor immunity, and eradicate metastatic sites.

SUMMARY

Embodiments described herein relate to lyophilized or freeze-dried plant virus-like particles as well as their therapeutic use in the treatment of cancer in a subject. The freeze drying process results in complete inactivation of the viral particle as well as ejection of viral genomic RNA from the viral capsid while retaining intact capsid formation. Advantageously, freeze dried plant virus-like particles can be formed from infectious plant viruses and have the same or substantially similar structural and biochemical characteristics as plant virus-like particles produced using bacterial derivation.

In some embodiments, a method of producing plant virus-like particles includes freeze drying an aqueous solution of plant virus particles. The freeze drying removes encapsulated RNA in the plant virus capsid thereby producing a substantially RNA-free plant virus-like particle. In some embodiments, the empty plant virus-like particles can have the same or a substantially similar structural and/or biochemical characteristics as the plant virus particle prior to freeze drying. In some embodiments, the similar biochemical characteristics can include tumor suppression. In some embodiments, the empty virus-like particles are non-infectious virus-like particles.

The plant virus particles can be derived from an infectious wild-type plant virus. In some embodiments, the plant virus particles can include picornavirus particles, such as a virus of the *Comovirus* genus. In some embodiments, the picornavirus particles can include cowpea mosaic virus (CPMV) particles. In some embodiments, a sample of plant virus particles can be obtained from the extract of a plant infected by the plant picornavirus.

In some embodiments, the aqueous solution of plant virus particles includes plant virus particles at a concentration of less than about 10 mg/ml, for example, about 9 mg/ml to about 0.1 mg/ml, about 5 mg/ml to about 0.1 mg/ml, about 2 mg/ml to about 0.1 mg/ml. The aqueous solution of the plant virus particles can be frozen at a temperature and for an amount of time that allows the plant virus particles to eject encapsulated genomic RNA while maintaining an intact capsid conformation. For example, the plant virus particles can be frozen at a temperature of about −5° C. to about −40° C., e.g., about −10° C. to about −30° C., for at least 1 day, 2 days, 3 days, 4 days or more to allow the plant virus particles to eject encapsulated genomic RNA while maintaining an intact capsid conformation. Following freezing, the frozen aqueous solution can be sublimated by heating the frozen solution at a temperature above freezing, e.g., above 0° C., and at a negative pressure, e.g., less than about 100 millibar, less than about 10 millibar, less than about 1 millibar, less than about 100 μbar. For example, the frozen aqueous solution of plant virus-like particles can be heated at a temperature of about 25° C. and at an ultimate chamber pressure of about 5 0ar.

In some embodiments, following freeze drying the method can further include contacting the freeze dried virus-like particles with an endoribonuclease, such as RNase (e.g., RNaseA), to degrade remaining viral nucleic acid. The RNase can be added to the freeze dried virus-like particles at a concentration of at least about 10 µg/ml, at least about 20 µg/ml, at least about 30 µg/ml, at least about 40 µg/ml, or at least about 50 µg/ml to degrade remaining viral nucleic acid.

Following endoribonuclease treatment, the endoribonuclease and degraded nucleic acids can be removed from the freeze dried virus-like particles by filtration and centrifugation.

In some embodiments, the freeze dried empty plant virus-like particles can be loaded with or coupled to a cargo molecule. In certain embodiments, the cargo molecule can include at least one of an anticancer agent, an antiviral agent, or an imaging agent.

Other embodiments described herein relate to methods of treating cancer in a subject in need thereof. The method can include administering in situ to cancer or tumor cells of the subject a therapeutically effective amount of freeze dried plant virus-like particles. In some embodiments, the freeze dried plant virus-like particles are administered in a pharmaceutically acceptable carrier. In some embodiments, the freeze dried plant virus-like particles are administered directly or proximal to cancer cells or tumor in the subject.

In some embodiments, the cancer is metastatic cancer. In some embodiments, the cancer is selected from the group consisting of melanoma, brain cancer, breast cancer, colon cancer, lung cancer, and ovarian cancer.

BRIEF DESCRIPTION OF THE DRAWINGS

FIG. 2(A-B) illustrate images and plots showing the characterization of RNA removal. (A) 1% (w/v) Agarose Gel stained with ethidium bromide (left) and Coomassie Brilliant blue (right). B) UV-vis spectra and results for CPMV, lyo-CPMV and lyo-eCPMV.

FIG. 3(A-B) illustrate a graphical representation of the characterization of particle integrity. A) Dynamic light scattering (DLS). DLS confirms that particles are intact and of appropriate size. The hydrodynamic radius ($R_h$) and the coefficient of variation (% Pd) are given for wild-type CPMV, lyo-CPMV and lyo-eCPMV. (B) Fast protein liquid chromatography (FPLC). FPLC chromatograms for all stages of purification. Lyo-CPMV no longer has a Gaussian peak shape, indicating ejected RNA. Peak symmetry is recovered upon removal of free RNA for lyo-eCPMV.

FIG. 4(A-B) illustrate cryo-electron micrographs of wild-type CPMV and Lyo-eCPMV. A) Wild-type CPMV particles appear dark in their interiors due to the presence of viral RNA. B) Lyo-eCPMV particles have lighter interiors and appear to be empty. Both particles appear largely intact and non-aggregated. Scale bar=200 Å.

FIG. 5(A-B) illustrate cryo-EM structure of lyo-eCPMV compared to structure of naturally occurring eCPMV. A) Cryo-EM structure of lyo-eCPMV at 17 Å resolution. B) Cryo-EM structure of naturally occurring eCPMV (EMD: 3562) shown filtered to 17 Å resolution. Scale bar=50 Å.

FIG. 6 (A-B) illustrate a graphical representation of significant delayed tumor progression and extended survival in mice treated with lyo-eCPMV particles. A) In situ injection of lyophilized CPMV (lyo-eCPMV) inhibited B16F10 melanoma growth. Lyophilized CPMV (100 µg) were injected intratumorally on days 0, 4, and 8 (n=4). A) Tumor growth curves shown as relative tumor volume. Data are means±SEM. Statistical significance was calculated by two-way ANOVA with Holm-Sidak test. *p>0.05; *p>0.0005; p>0.0001. Growth curves were stopped when the first animal of the corresponding group was sacrificed (tumor volume≥1500 mm³). B) Survival rates of treated and control mice. Statistical significance was calculated by Log-rank test. p<0.01.

DETAILED DESCRIPTION

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

The term "about" when referring to a measurable value such as an amount, a temporal duration, and the like, is meant to encompass variations of ±20% or 110%, more preferably ±5%, even more preferably ±1%, and still more preferably ±0.1% from the specified value, as such variations are appropriate to perform the disclosed methods.

The term "agent" is used herein to denote a chemical compound, a mixture of chemical compounds, a biological macromolecule, or an extract made from biological materials.

The term "bioactive agent" can refer to any agent capable of promoting a biological effect, e.g., alters or modulates a biological function of a physiological target substance. By "alters" or "modulates a biological function" herein is meant that the physiological target undergoes a change in either the quality or quantity of its biological activity; this includes increases or decreases in activity. Thus, bioactive agents include a wide variety of drugs, including antagonists, for example enzyme inhibitors, and agonists, for example a transcription factor which results in an increase in the expression of a desirable gene product (although as will be appreciated by those in the art, antagonistic transcription factors may also be used), are all included.

In addition, a "bioactive agent" includes those agents capable of direct toxicity and/or capable of inducing toxicity towards healthy and/or unhealthy cells in the body. Also, the bioactive agent may be capable of inducing and/or priming the immune system against potential pathogens. A number of mechanisms are possible including without limitation, (i) a radioisotope linked to a protein as is the case with a radiolabled protein, (ii) an antibody linked to an enzyme that metabolizes a substance, such as a produg, thus rendering it active in vivo, (iii) an antibody linked to a small molecule therapeutic agent, (iv) a radioisotope, (v) a carbohydrate, (vi) a lipid, (vii) a thermal ablation agent, (viii) a photosensitizing agent, and (ix) a vaccine agent.

The terms "biocompatible" and "biologically compatible" refer to materials that are, along with any metabolites or degradation products thereof, generally non-toxic to the recipient, and do not cause any significant adverse effects to the recipient, at concentrations resulting from the degradation of the administered materials. Generally speaking, biocompatible materials are materials that do not elicit a significant inflammatory or immune response when administered to a patient.

The term "cargo molecule," refers to a small organic or inorganic bioactive agent, such as a drug or imaging agent that can be associated with a viral nanoparticle in order to confer an additional function on the viral nanoparticle.

The term "effective amount" refers to an amount of virus-like particles, cargo molecules, and/or bioactive agents that is sufficient to provide a desired effect. An effective amount in any individual case may be determined by one of ordinary skill in the art using routine experimentation.

The term "imaging agent" can refer to a biological or chemical moiety capable being linked and/or conjugated directly or indirectly to nanoparticle constructs described herein and that may be used to detect, image, and/or monitor the presence and/or progression of a cell cycle, cell function/physiology, condition, pathological disorder and/or disease.

The term "subject" can be a human or non-human animal. Non-human animals include, for example, livestock and pets, such as ovine, bovine, porcine, canine, feline and murine mammals, as well as reptiles, birds and fish. Preferably, the subject is human.

The terms "virus" and "virus particle" are used interchangeably herein. Virus particles include a number of capsid proteins that are assembled to form a protein cage, within which is the nucleic acid encoding the virus. Note that the viruses and virus particles described herein are presumed to include a nucleic acid within the protein cage, unless specifically stated to the contrary. While the nucleic acid will typically be the nucleic acid encoding the virus, in some embodiments the viral nucleic acid may have been replaced with exogenous nucleic acid. In some embodiments, the nucleic acid is RNA, while in other embodiments the nucleic acid is DNA.

Embodiments described herein relate to lyophilized or freeze dried plant viral-like particles as well as their therapeutic use in the treatment of cancer in a subject. It was discovered that freeze drying a plant virus particle results in complete inactivation of the virus particle as well as ejection of viral genomic RNA from the viral capsid while retaining intact capsid formation. Advantageously, freeze dried virus-like particles can be formed from an infectious plant virus without using agroinfiltration methods that employ a plasmid based expression system. The freeze drying process described herein allows virus-like particles to retain the same or substantially similar structural (e.g., size, shape, and morphology) and biochemical characteristics (e.g., immune response and anti-cancer efficacy) as bacterially derived plant virus-like particles without introducing immunostimulatory contaminants, such as lipopolysaccharide (LPS), produced during bacterial infiltration.

In some embodiments, where the freeze dried virus-like particles are used for therapeutic applications, the particles can be administered to a site of interest, such as a cell or tissue of a subject. In other embodiments, where the freeze dried virus-like particles are used for agricultural applications, the site of interest can be a plant propagation material, a plant, part of a plant and/or plant organ.

Plant virus particles used to produce empty plant virus-like particles as described herein can include wild-type plant viruses. In certain embodiments, the wild-type plant virus can include cowpea mosaic virus (CPMV). Wild-type plant viruses can be obtained, for example, through established procedures of plant virus production including plant inoculation, propagation, and purification. In some embodiments, a sample of plant virus in a buffer solution can be filtered into deionized water through a centrifugal filter to remove salts and low molecular weight impurities.

In order to produce freeze dried plant virus-like particles, an aqueous solution or suspension of plant virus particles can be frozen at a temperature and for an amount of time that allows the virus to eject the encapsulated genomic RNA while maintaining an intact capsid conformation. In various embodiments, an aqueous solution of plant virus particles can be slowly frozen over a duration of time of at least 1 day, at least 2 days, at least 3 days, at least 4 days, at least 5 days, at least 6 days or more at a temperature of about of about $-5°$ C. to about $-40°$ C., e.g., about $-10°$ C. to about $-30°$ C., about $-15°$ C. to about $-25°$ C., or about $-20°$ C. to allow ejection of the encapsulated genomic RNA from a plant virus. In certain embodiments, an aqueous solution of the wild-type plant virus CPMV is slowly frozen for at least about 4 days at a temperature greater than $-30°$ C. or greater than $-25°$ C. prior to sublimation.

For example, a wild-type plant virus aqueous solution can be frozen at $-20°$ C. for about 4 days to remove the virus's genomic RNA. Typical freezing procedures using liquid $N_2$ are unable to eject genomic RNA. Without being bound by theory, it is believed that the freeze drying process leads to disruption between the genomic RNA and coat protein of the virus and as the osmolyte concentration increases, so too does the internal pressure within the viral capsid. It is further believed that these effects both destabilize RNA binding and lead to ejection of the RNA from the virus capsid.

The concentration of the plant virus particles in the aqueous solution or suspension during freezing can be controlled to obtain a sufficient yield of empty plant virus-like particles. For example, at concentrations higher than about 10 mg/ml, plant virus like particles aggregate and significant fractions are unable to resuspend following lyophilization. Therefore, in particular embodiments, the plant virus particles are frozen in an aqueous solution at a concentration less than about 10 mg/ml, for example, about 9 mg/ml to about 0.1 mg/ml, about 5 mg/ml to about 0.1 mg/ml, about 2 mg/ml to about 0.1 mg/ml. In some embodiments, the plant virus can be frozen as described herein at a concentration of about 1 mg/ml.

In some embodiments, the frozen aqueous solution of the plant virus particles can be annealed by increasing or decreasing the temperature to facilitate crystallization and destabilize RNA in the virus capsid. The freezing temperature can be cycled with a range of temperatures that range from about $-40°$ C. to 25° C., or from in freezing temperatures of about $-40°$ C. to $-5°$ C.

Freezing as part of the freeze drying process to produce plant virus-like particles can take place in a freeze dryer or in a separate freezer prior to the process of sublimation. Following freezing and ejection of genomic RNA from the virus-like particles, the virus-like particles can be dried or sublimated to form the freeze dried virus-like particles. The frozen virus solution typically goes from a frozen state without thawing first to a dry powder through the process of sublimation. The pressure surrounding the frozen aqueous plant virus particles can be reduced to allow frozen water in the solution to sublimate directly from the solid phase to the gas phase. This freeze drying process results in a dry powder.

Any sublimation modality can be employed in a method described herein. For example, a suitable modality can include a closed tray in a sublimation chamber. In some embodiments, the plant virus-like particles are sublimated for at least about 4 days at negative pressure to achieve complete dehydration and RNA ejection. In some embodiments, sublimation of the frozen aqueous solution includes heating the frozen solution at a temperature above freezing, e.g., above 0° C., above about 10° C., above about 15° C., above about 20° C., above about 25° C., or about 15° C. to about 30° C. and at a negative pressure, e.g., less than about 100 millibar, less than about 10 millibar, less than about 1 millibar, less than about 100 μbar. For example, the frozen aqueous solution of plant virus-like particles can be sublimated at a temperature of about 25° C. and at an ultimate chamber pressure of about 5 0ar.

Examples of components of freeze drying/sublimation equipment that can be used in a method described herein can include, but are not limited to, a refrigeration system, a vacuum system, a control system, product chamber or manifold, and a condenser. The refrigeration system can be employed to cool a condenser located inside the freeze dryer. The refrigeration system can also be employed to cool shelves in the product chamber for the freezing of the product. The vacuum system can include a separate vacuum pump connected to an airtight condenser and attached product chamber to reduce the pressure surrounding the sample.

Typical control systems vary in complexity and usually include temperature and pressure sensing ability. Advanced controllers will allow the programming of a complete process for freeze drying and will include options to monitor how the freeze drying process is progressing. Choosing a control system for the freeze dryer can depend on the application and use (i.e., medical lab vs. agricultural production).

Product chambers are typically either a manifold with attached flasks, or, a larger chamber with a system of shelves on which to place the product. The purpose of the condenser is to attract the vapors being sublimed off of the product. Because the condenser is maintained at a lower energy level relative to the product ice, the vapors condense and turn back into solid form (ice) in the condenser. The sublimated ice accumulates in the condenser and can be manually removed at the end of the freeze drying cycle (defrost step). The condenser temperature required is dictated by the freezing point and collapse temperature of the product. The refrigeration system must be able to maintain the temperature of the condenser substantially below the temperature of the product.

Freeze dryers for use in a method described herein can be informally classified by the type of product chamber: (1) manifold dryers where the product is typically pre-frozen & in flasks; (2) shelf dryers where the product is placed in a tray or directly on a shelf; and (3) combination units with both drying options. In shelf freeze dryers, the condenser can be located inside the product chamber (internal condenser) or in a separate chamber (external condenser) connected to the product chamber by a vapor port. Manifold freeze dryers rely on ambient conditions to provide the heat of sublimation to the product. This heat input does not melt the product because an equivalent amount of heat is removed by vaporization of the solvent. Advanced shelf freeze dryers can provide a heat source to control/expedite the drying process and they can also employ the refrigeration system to allow freezing of product inside the unit.

Following sublimation of the frozen aqueous solution of plant virus particles, the resulting dry powder can include a mixture of RNA, intact RNA-free empty virus-like particles and a small amount of protein aggregates. In some embodiments, the lyophilized plant virus-like particle products produced during the freeze drying process are extremely hydroscopic. Therefore, in certain embodiments, the lyophilized plant virus-like particle products are sealed in air tight containers following freeze drying to prevent rehydration from atmospheric exposure.

The lyophilized plant virus like particles produced during the freeze drying process can be resuspended into a buffered solution and aggregates can be removed using standard methods such as centrifugation and decanting. In an exemplary embodiment, a lyophilized powder of the plant virus like particles can be resuspended using 0.01 M phosphate buffer (pH 7.0).

The resuspended virus-like particle solution can be further treated to remove any remaining nucleic acid from the virus-like particles, such as genomic RNA. For example, a sample of resuspended virus like particles can be treated with endoribonuclease, such as RNase (e.g., RNaseA, to degrade remaining viral nucleic acid in the solution. The RNase can be added to the freeze dried virus-like particles at a concentration of at least about 10 μg/ml, at least about 20 μg/ml, at least about 30 μg/ml, at least about 40 μg/ml, or at least about 50 μg/ml to degrade remaining viral nucleic acid.

Following endoribonuclease treatment, the endoribonuclease and degraded nucleic acids can be removed from the freeze dried virus-like particles by filtration and centrifugation. For example, degraded nucleic acid can be removed using diafiltration with 100 kDa molecular weight cut-off centrifugal filters. In an example of a method described herein, empty CPMV virus like particles were recovered at a yield of 0.8 g of particles/1 kg infected leaf tissue.

The freeze dried, endoribonuclease treated, virus like particles can be empty virus-like particles. By empty virus-like particles it is meant the virus-like particles are substantially free of nucleic acids (e.g., RNA). In some embodiments, the substantially RNA-free virus-like particles are at least 95% RNA-free, at least 96% RNA-free, at least 97% RNA-free, at least 98% RNA-free, at least 99% RNA-free, at least 99.9% RNA-free, or at least 99.99% RNA-free.

Following freeze drying, endoribonuclease degradation, and filtration, the freeze dried plant virus-like particles can be assessed using one more assays to determine purity and/or genomic RNA content. In an exemplary embodiment, empty VLPs produced in accordance with a method described herein can be assayed using UV-Vis spectroscopy (see FIG. 2B) where the two absorbance intensities (i.e., A260/A280) are indicative of RNA presence in a sample of freeze-dried plant virus-like particles. In some embodiments, freeze-dried VLPs produced in accordance with a method described herein can have an A260/A280 ratio range of about 0.69 to about 0.90. In one example, the A260/A280 ratio is about 0.80.

Figure 2A:
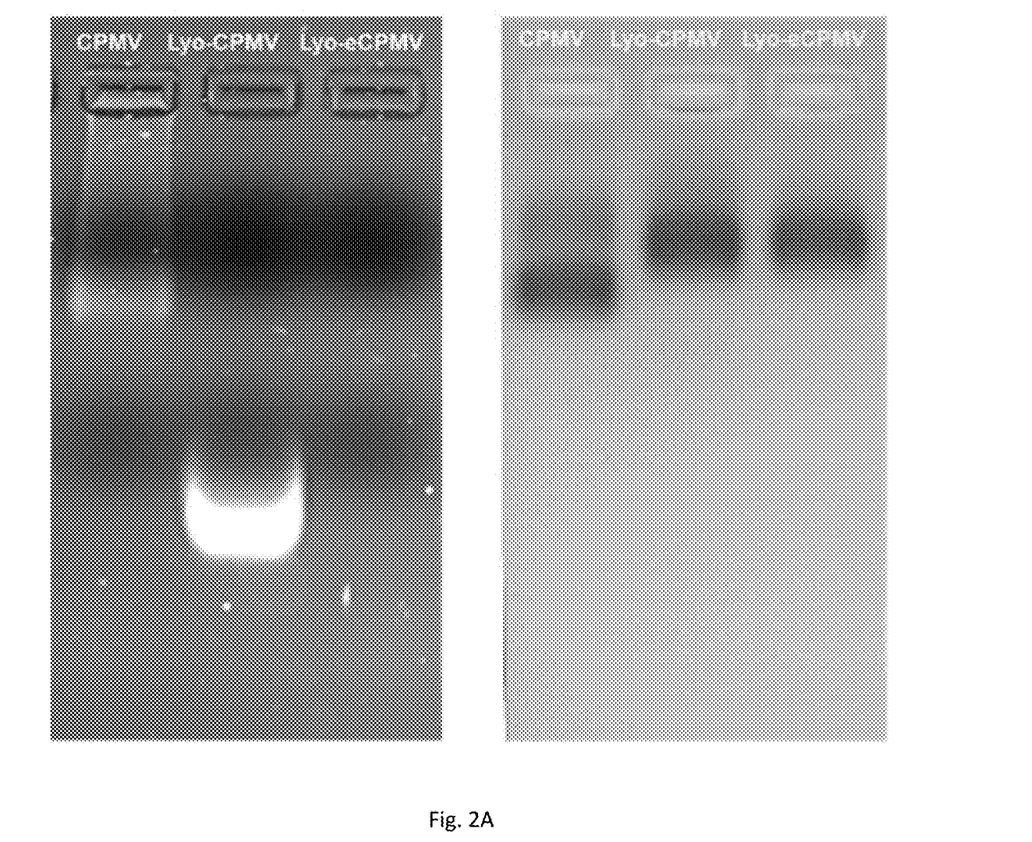
Figure 2B:
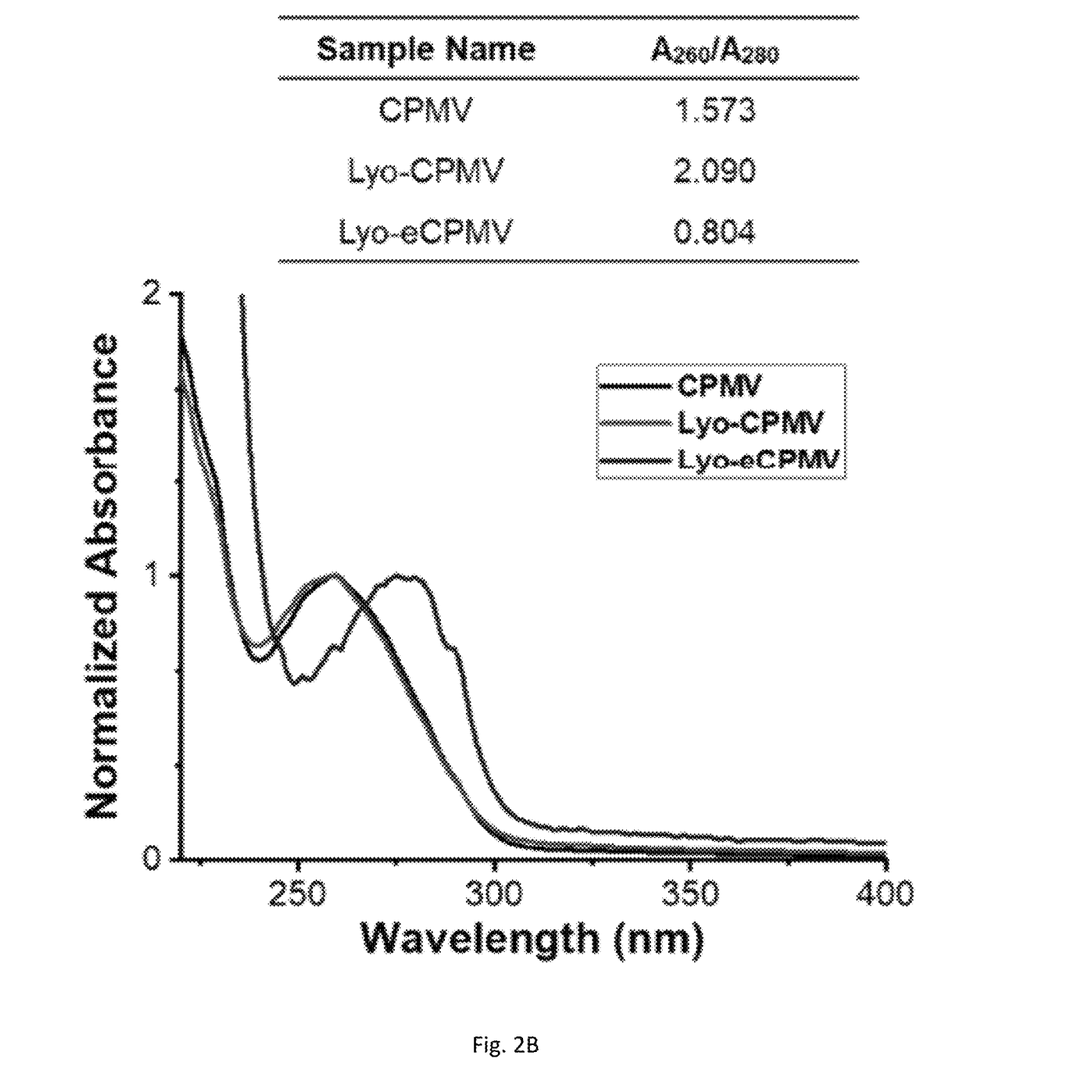
Figure 3A:
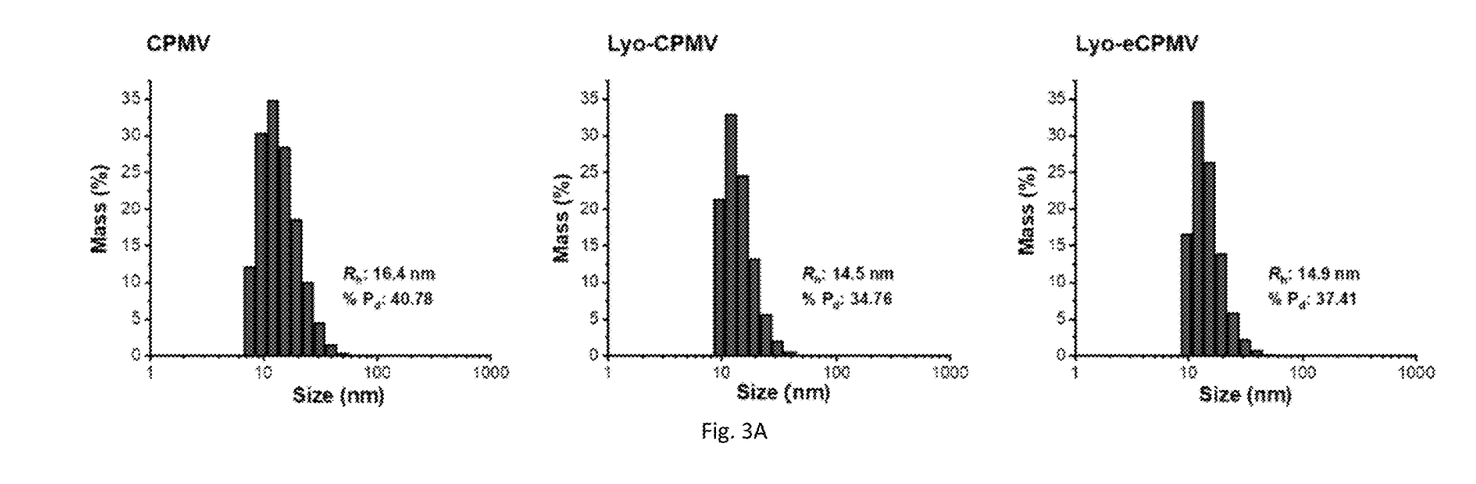
Figure 3B:
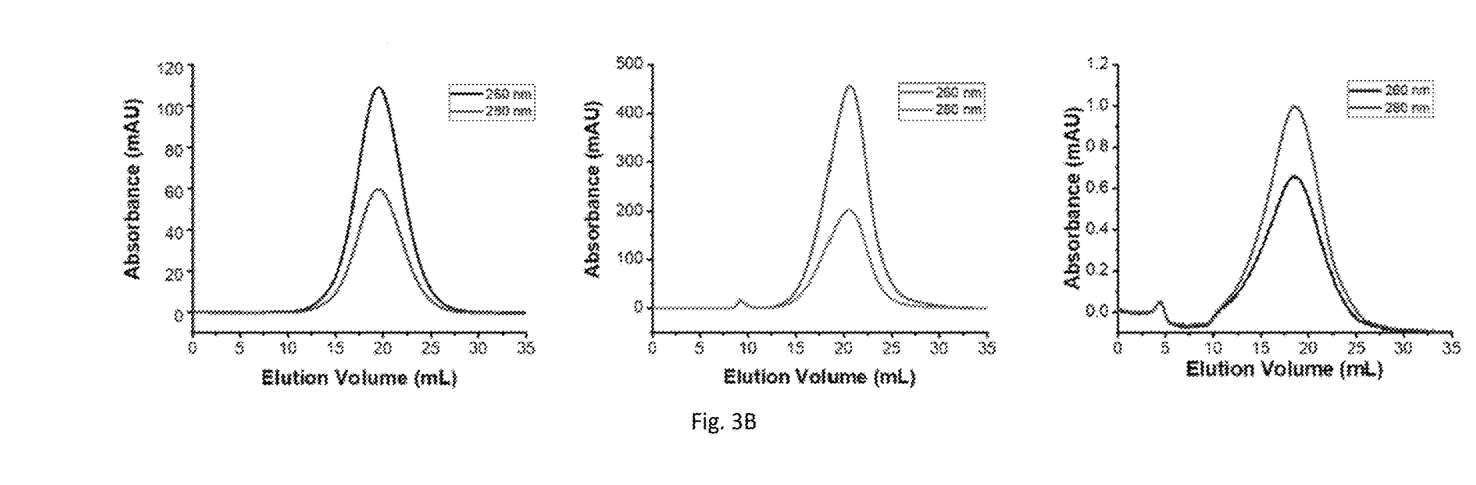

Additional assays to determine the purity and/or genomic RNA content include but are not limited to dynamic light scattering (DLS) and fast protein liquid chromatography (FPLC), agarose gel electrophoresis with ethidium bromide (EtBr) (See for example, FIGS. 2A, and 3A and B).

The freeze dried plant virus-like particles can be produced using a variety of different types of plant viruses. Plant viruses used to produce the freeze dried plant virus-like particles as described herein can be categorized based on their source and structure. One advantage of using viruses from plant sources is that they can be readily cultivated, and are unlikely to cause infection when used in vivo in a mammalian subject. In addition, viruses having a helical, icosahedral, or prolate structure can be used.

In some embodiments, the plant virus can be an icosahedral plant virus. Examples of icosahedral plant viruses include the virus families Geminiviridae, Luteoviridae, Bromoviridae, Phycodnaviridae, and Picornaviridae. In some embodiments, the icosahedral plant virus is from the family Picornaviridae. Plant picornaviruses are relatively small, non-enveloped, positive-stranded RNA viruses with an icosahedral capsid. Plant picornaviruses have a number of additional properties that distinguish them from other picornaviruses, and are categorized as the subfamily secoviridae. In some embodiments, the plant virus is selected from the Comovirinae virus subfamily. Examples of viruses from the Comovirinae subfamily include Cowpea mosaic virus, Broad bean wilt virus 1, and Tobacco ringspot virus. In a particular embodiment, the freeze dried virus-like particles are produced from virus of the genus *Comovirus*. In some embodiments, the comovirus is a cowpea mosaic virus (CPMV).

The wild-type virus for the production of the freeze dried VLPs can be obtained according to various methods known to those skilled in the art. In some embodiments, the virus particles can be obtained from the extract of a plant infected by the plant virus. For example, cowpea mosaic virus can be grown in black eyed pea plants, which can be infected within 10 days of sowing seeds. Plants can be infected by, for example, coating the leaves with a liquid containing the virus, and then rubbing the leaves, preferably in the presence of an abrasive powder which wounds the leaf surface to allow penetration of the leaf and infection of the plant. Within a week or two after infection, leaves are harvested and viral nanoparticles are extracted. In the case of cowpea mosaic virus, 100 mg of virus can be obtained from as few as 50 plants. Procedures for obtaining plant picornavirus particles using extraction of an infected plant are known to those skilled in the art. See Wellink J., Meth Mol Biol, 8, 205-209 (1998). Procedures are also available for obtaining virus-like particles. Saunders et al., Virology, 393(2):329-37 (2009). The disclosures of both of these references are incorporated herein by reference.

In some embodiments, the freeze dried empty virus-like particles produced in accordance with a method described herein can be loaded with one or more cargo molecules and/or bioactive agents. For example, the cargo molecule and/or bioactive agent can be loaded by covalently attaching the cargo molecule and/or bioactive agent to a reactive molecule on a surface (interior or exterior) of one or more freeze dried virus like particles.

A variety of different types of cargo molecules and/or bioactive agents can be loaded into or onto the freeze dried virus-like particles. Cargo molecules and/or bioactive agents are generally relatively small organic or inorganic molecules. In some embodiments, the cargo molecules have a molecular weight ranging from about 50 to about 5000 daltons, with some embodiments being directed to cargo molecules having a weight ranging from about 50 to about 1000 daltons, or from about 100 to about 500 daltons. Examples of cargo molecules are imaging agents and therapeutic agents such as antitumor agents.

In some embodiments, the freeze dried virus-like particle is modified to carry an imaging agent. Examples of imaging agents include fluorescent compounds, radioactive isotopes, and MRI contrast agents. For example, in some embodiments, the imaging agent is a fluorescent molecule for fluorescent imaging. The imaging agent can be any material having a detectable physical or chemical property. Such imaging agents have been well-developed in the field of fluorescent imaging, magnetic resonance imaging, positive emission tomography, or immunoassays and, in general, most any imaging agent useful in such methods can be applied to the present invention. Thus, an imaging agent is any composition detectable by spectroscopic, photochemical, biochemical, immunochemical, electrical, optical or chemical means. Means of detecting imaging agents are well known to those of skill in the art. Thus, for example, where the imaging agent is a radioactive compound, means for detection include a scintillation counter or photographic film as in autoradiography. Where the imaging agent includes a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label.

Examples of imaging agents that can be used include magnetic beads (e.g., Dynabeads), fluorescent dyes (e.g., fluorescein isothiocyanate, AlexaFluor555, Texas red, rhodamine, and the like), radiolabels (e.g., $^{3}H$, $^{14}C$, $^{35}S$, $^{125}I$, $^{121}I$, $^{112}I$, $^{99m}Tc$), other imaging agents such as microbubbles (for ultrasound imaging), $^{18}F$, $^{11}C$, $^{15}O$, (for Positron emission tomography), $^{99m}TC$, $^{111}In$ (for single photon emission tomography), and chelated lanthanides such as terbium, gadolinium (e.g., chelated gadolinium), and europium or iron (for magnetic resonance imaging). The choice of imaging agent depending on sensitivity required, ease of conjugation with the compound, stability requirements, available instrumentation, and disposal provisions.

In some embodiments, the imaging agent is a magnetic resonance imaging agent. Disease detection using MRI is often difficult because areas of disease have similar signal intensity compared to surrounding healthy tissue. In the case of magnetic resonance imaging, the imaging agent can also be referred to as a contrast agent. Lanthanide elements are known to be useful as contrast agents. The lanthanide chemical elements comprises the fifteen metallic chemical elements with atomic numbers 57 through 71, and include lanthanum, cerium, praseodymium, neodymium, promethium, samarium, europium, gadolinium, terbium, dysprosium, holmium, erbium, thulium, ytterbium, and lutetium. Preferred lanthanides include europium, gadolinium, and terbium. In order to more readily handle these rare earth metals, the lanthanides are preferably chelated. In some embodiments, the lanthanide selected for use as a contrast agent is gadolinium, or more specifically gadolinium (III). Gadolinium contrast agents are generally chelated to facilitate attachment to the virus particle. Examples of effective gadolinium chelating molecules include 1,4,7,10-tetraazacyclododecane-1,4,7,10-tetraacetic acid (DOTA), diethylenetriaminopentacetate (DTPA), 1,4,7,10-tetraazacyclododecane-1,4,7-triasacetic acid (DO3A), 6-amino-6-methylperhydro-1,4-diazepinetetraacetic acid (AAZTA), and 4-carboxyamido-3,2-hydroxypyridinone (HOPA).

In other embodiments, the cargo molecule and/or bioactive agent can be a therapeutic agent. Examples of therapeutic agents include cardiovascular drugs (e.g., antihypertensive drugs, antiarrhythmic agents, and diuretics), neuropharmaceuticals (e.g., analgesics, anesthetics, and antipsychotics), gastrointestinal drugs (e.g., anti-ulcer drugs, antiemetics, and gastroprokinetic agents), respiratory tract agents (e.g., anthasthamtic or antiallergic drugs), antiinfective agents (antibiotics, antimycotics, and antiviral agents), endocrine-affecting drugs (e.g., steroids, hormones, and contraceptives), anti-inflammatory drugs, immunosuppressant drugs, and antitumor agents.

In some embodiments, the therapeutic agents used as cargo molecules are small molecule antitumor agents. One advantage of using antitumor agents as cargo molecules is the ability of viral nanoparticles to preferentially associate with tumor cells. Examples of small molecule antitumor agents include angiogenesis inhibitors such as angiostatin K1-3, DL-α-difluoromethyl-ornithine, endostatin, fumagillin, genistein, minocycline, staurosporine, and thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, deguelin, 5,6-dichlorobenz-imidazole 1-beta-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin-.alpha., rapamycin, thapsigargin, and bikunin, and derivatives thereof.

In other embodiments, the cargo molecule is an antiviral agent. It has been shown that plant picornaviruses such as cowpea mosaic virus have a natural affinity for certain cells of the immune system such as macrophages and dendritic cells, which can be the natural target for viruses such as cowpea mosaic virus. Accordingly, freeze dried processed virus-like particles described herein can be loaded with cargo molecule and will naturally deliver antiviral agent to macrophages and dendritic cells. Examples of antiviral agents include abacavir, acyclovir, adefovir, amantadine, amprenavir, ampligen, arbidol, atazanavir, atripla, balavir, boceprevirertet, cidofovir, combivir, dolutegravir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon types I-III, lamivudine, lopinavir, loviride, maraviroc, moroxydine, methisazone, nelfinavir, nevirapine, nexavir, oseltamivir (Tamiflu), peginterferon alfa-2a, penciclovir, peramivir, PF-429242, pleconaril, podophyllotoxin, raltegravir, ribavirin, rimantadine, ritonavir, pyramidine, saquinavir, sofosbuvir, stavudine, tea tree oil, telaprevir, tenofovir, tenofovir disoproxil, tipranavir, trifluridine, trizivir, tromantadine, truvada, traporved, valaciclovir (Valtrex), valganciclovir, vicriviroc, vidarabine, viramidine, zalcitabine, zanamivir (Relenza), and zidovudine The cargo molecules and/or bioactive agents can be loaded into and/or conjugated to the freeze dried plant virus-like particles by any suitable technique, with appropriate consideration of the need for pharmacokinetic stability and reduced overall toxicity to the patient. The term "conjugating" when made in reference to an agent and a nanoparticle construct as used herein means covalently linking the agent to virus like particles subject to the limitation that the nature and size of the agent and the site at which it is covalently linked to the virus like particles do not interfere with the distribution of the virus like particles. The cargo molecule can be linked to the interior or the exterior of virus like particles, while in some embodiments the cargo molecule is linked to both the interior and the exterior of the virus like particles. In some embodiments, where the cargo molecule is linked to a freeze dried processed empty virus like particle, the location of the cargo molecule on the interior or exterior is governed by the amino acids of viral coat proteins that are selected as reactive sites.

Cargo molecules and/or bioactive agents can be coupled to the freeze dried virus-like particles either directly or indirectly (e.g., via a binder group). In some embodiments, the molecule and/or agent is directly attached to a functional group capable of reacting with the agent and/or molecule. For example, viral coat proteins include lysines that have a free amino group that can be capable of reacting with a carbonyl-containing group, such as an anhydride or an acid halide, or with an alkyl group containing a good leaving group (e.g., a halide). Viral coat proteins also contain glutamic and aspartic acids. The carboxylate groups of these amino acids also present attractive targets for functionalization using carbodiimide activated linker molecules; cysteines can also be present which facilitate chemical coupling via thiol-selective chemistry (e.g., maleimide-activated compounds). Further, viral coat proteins contain tyrosines, which can be modified using diazonium coupling reactions. In addition, genetic modification can be applied to introduce any desired functional residue, including non-natural amino acids, e.g., alkyne- or azide-functional groups. See Hermanson, G. T. Bioconjugation Techniques. (Academic Press, 2008) and Pokorski, J. K. and N. F. Steinmetz, Mol Pharm 8(1): 29-43 (2011), the disclosures of which are incorporated herein by reference.

In other embodiments, a chemical binder group can be used. A binder group can serve to increase the chemical reactivity of a substituent on either the agent or freeze dried virus-like particles, and thus increase the coupling efficiency. Binder chemistries can include maleimidyl binders, which can be used to bind to thiol groups, isothiocyanate and succinimidyl (e.g., N-hydroxysuccinimidyl (NHS)) binders, which can bind to free amine groups, diazonium which can be used to bind to phenol, and amines, which can be used to bind with free acids such as carboxylate groups using carbodiimide activation. Useful functional groups are present on viral coat proteins based on the particular amino acids present, and additional groups can be designed into recombinant viral coat proteins. It will be evident to those skilled in the art that a variety of bifunctional or polyfunctional reagents, both homo- and hetero-functional (such as those described in the catalog of the Pierce Chemical Co., Rockford, Ill.), can be employed as a binder group. Coupling can be effected, for example, through amino groups, carboxyl groups, sulfhydryl groups or oxidized carbohydrate residues.

Other types of binding chemistries are also available. For example, methods for conjugating polysaccharides to peptides are exemplified by, but not limited to coupling via alpha- or epsilon-amino groups to NaIO$_4$-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide binder wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to plant virus peptides are described by U.S. Pat. No. 7,666,624.

In some embodiments, the surface of the freeze dried virus-like particles can be modified by attachment of something other than a cargo molecule. For example, the freeze dried processed virus-like particle can be modified to include PEGylation, cell penetrating peptides, or targeting molecules. The virus-like particles can be modified either before loading the virus-like particles with cargo molecules or after loading with cargo molecules. Targeting molecules can be attached to the outside of the freeze dried virus-like particles in order to guide the virus-like particles to a particular target tissue, such as tumor tissues. Examples of targeting molecules include peptide ligands (e.g., RGD, bombesin, or GE11), vitamins such as folic acid, and other tumor-homing proteins such as transferrin, as well as and antibodies such as Herceptin or any other antibody or antibody fragment with tumor-specific properties, and DNA-, RNA-, or PNA-based aptamers that specifically bind to an antigen present on the target tissue, such as a tumor antigen. Cell penetrating peptides can also be attached to the outside of the virus-like particles to encourage internalization of the virus like particles constructs. Cell penetrating peptides are generally relatively short, amphipathic peptides. Examples of cell penetrating peptides include TAT sequence or polyArginine peptides.

In some embodiments, rather than covalent attachment, cargo molecules and/or bioactive agents can also be loaded into or onto the freeze dried virus-like particles by non-covalent intermolecular interactions between the compound and the particles, such as hydrogen bonding, electrostatic interactions, hydrophobic interactions, and Van der Waals forces.

In some embodiments, a targeting molecule can also be attached to the freeze dried plant virus-like particles. By "targeting molecule" herein is meant a molecule which serves to target or direct the plant virus-like particles released to a particular location, cell type, diseased tissue, or association. In general, the targeting molecule is directed against an antigenic site. Thus, for example, antibodies, cell surface receptor ligands and hormones, lipids, sugars and dextrans, alcohols, bile acids, fatty acids, amino acids, peptides and nucleic acids may all be attached to localize or target the virus-like particles to a particular site. In some embodiments, the targeting molecule allows targeting of the plant virus-like particles to a particular tissue or the surface of a cell.

In some embodiments, the targeting molecule is a peptide. For example, chemotactic peptides have been used to image tissue injury and inflammation, particularly by bacterial infection; see WO 97/14443, hereby expressly incorporated by reference in its entirety. Another example, are peptides specific to fibrin or vascular cell adhesion molecules to direct the imaging probe to sites of inflammation, such as an atherosclerotic plaque. In other embodiments, the targeting molecule is an antibody. The term "antibody" includes antibody fragments, as are known in the art, including Fab Fab$_2$, single chain antibodies (Fv for example), chimeric antibodies, etc., either produced by the modification of whole antibodies or those synthesized de novo using recombinant DNA technologies. In further embodiments, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin.

In some embodiments, the antibody is directed against a cell-surface marker on a cancer cell; that is, the antigenic site is a cell surface molecule. As is known in the art, there are a wide variety of antibodies and antibody fragments known to be differentially expressed on tumor cells, including, but not limited to, HER2. Examples of physiologically relevant carbohydrates may be used as cell-surface markers include, but are not limited to, antibodies against markers for breast cancer (CA 15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

In some embodiments, the targeting molecule is all or a portion (e.g., a binding portion) of a ligand for a cell surface receptor. Suitable ligands include, but are not limited to, all or a functional portion of the ligands that bind to a cell surface receptor selected from the group consisting of insulin receptor (insulin), insulin-like growth factor receptor (including both IGF-1 and IGF-2), growth hormone receptor, glucose transporters (particularly GLUT 4 receptor), transferrin receptor (transferrin), epidermal growth factor receptor (EGF), low density lipoprotein receptor, high density lipoprotein receptor, leptin receptor, estrogen receptor (estrogen); interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor (VEGF), PDGF receptor (PDGF), transforming growth factor receptor (including TGF-α and TGF-β), EPO receptor (EPO), TPO receptor (TPO), ciliary neurotrophic factor receptor, prolactin receptor, and T-cell receptors. Receptor ligands include ligands that bind to receptors such as cell surface receptors, which include hormones, lipids, proteins, glycoproteins, signal transducers, growth factors, cytokines, and others.

In some embodiments, the freeze dried plant virus-like particle can be administered, injected, or implanted in a minimally invasive fashion in a subject in need thereof to treat diseases (e.g., cancer) and/or disorder in the subject. In particular embodiments, the freeze dried processed virus-like particles can be in situ delivered and/or administered to the tissue of the subject. Upon delivery and/or administration of the virus-like particles to tissue, the virus like particles can preferentially accumulate in diseased tissue, such as cancer tissue or inflamed tissue (e.g., atherosclerotic blood vessels). While not intending to be bound by theory, it appears that plant viral-like nanoparticles can be taken up by blood components such as macrophage cells of the immune system, which subsequently accumulate in diseased tissue (e.g., a tumor or atherosclerotic blood vessel), thereby delivering the virus-like particle to cells at the disease site.

In some embodiments, administering the freeze dried plant virus-like particle to a subject can generate an immune response in the subject. An "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, invading pathogens, cells or tissues infected with pathogens, or, in cases of autoimmunity or pathological inflammation, normal human cells or tissues. Components of an immune response can be detected in vitro by various methods that are well known to those of ordinary skill in the art.

Other embodiments described herein relate to methods of treating cancer in a subject in need thereof by administering in situ to cancer of the subject a therapeutically effective amount of the freeze dried plant virus-like particles produced as described herein. While not intending to be bound by theory, it appears that freeze dried plant virus-like particles have an anticancer effect as a result of eliciting an immune response to the cancer similar to plant virus-like particles produced by agroinfiltration.

"Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression. Examples of cancers are sarcoma, breast, lung, brain, bone, liver, kidney, colon, and prostate cancer. In some embodiments, the freeze dried processed virus-like particles are used to treat cancer selected from the group consisting of but not limited to melanoma, breast cancer, colon cancer, lung cancer, and ovarian cancer. In some embodiments, the freeze dried processed virus-like particles described herein are used to treat invasive melanoma.

In some embodiments, the in situ administration of the freeze dried plant virus-like particles can be proximal to a tumor in the subject or directly to the tumor site (e.g., intratumoral injection) to provide a high local concentration of the plant virus-like particles in the tumor microenvironment. The method represents a type of in situ vaccination, in which application of an immunostimulatory reagent directly or proximal to the tumor modifies the tumor microenvironment so that the immune system is able to respond to the tumor. For example, the cowpea mosaic virus-like particle has been shown to stimulate an anti-tumor response through recruitment of monocytes into a tumor microenvironment (TME), promotes signaling of the IFN-gamma pathway, and/or increase recruitment of TINs and natural killer cells.

In some embodiments, a therapeutic method for the treatment of cancer in a subject can be described herein can further include the step of ablating the cancer. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, immunotherapy, and administration of immunotoxins.

In some embodiments, the step of ablating the cancer includes administering a therapeutically effective amount of an anticancer agent to the subject. Examples of anticancer agents include angiogenesis inhibitors such as angiostatin K1-3, DL-α-difluoromethyl-ornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin, rapamycin, thapsigargin, and bikunin, and derivatives (as defined for imaging agents) thereof.

In some embodiments, the step of ablating the cancer includes immunotherapy of the cancer. Cancer immunotherapy is based on therapeutic interventions that aim to utilize the immune system to combat malignant diseases. It can be divided into unspecific approaches and specific approaches. Unspecific cancer immunotherapy aims at activating parts of the immune system generally, such as treatment with specific cytokines known to be effective in cancer immunotherapy (e.g., IL-2, interferon's, cytokine inducers).

When used in vivo, the freeze dried plant virus-like particles can be administered as a pharmaceutical composition, and a pharmaceutically acceptable carrier. The freeze dried virus-like particles, or pharmaceutical compositions comprising these freeze dried virus-like particles, may be administered by any method designed to provide the desired effect. Administration may occur enterally or parenterally; for example orally, rectally, intracisternally, intravaginally, intraperitoneally or locally. Parenteral administration methods include intravascular administration (e.g., intravenous bolus injection, intravenous infusion, intra-arterial bolus injection, intra-arterial infusion and catheter instillation into the vasculature), peri- and intra-target tissue injection, subcutaneous injection or deposition including subcutaneous infusion (such as by osmotic pumps), intramuscular injection, intraperitoneal injection, intracranial and intrathecal administration for CNS tumors, and direct application to the target area, for example by a catheter or other placement device.

One skilled in the art can readily determine an effective amount of the freeze dried plant virus-like particles to be administered to a given subject, by taking into account factors such as the size and weight of the subject; the extent of disease penetration; the age, health and sex of the subject; the route of administration; and whether the administration is local or systemic. Those skilled in the art may derive appropriate dosages and schedules of administration to suit the specific circumstances and needs of the subject. For example, suitable doses of the virus particles to be administered can be estimated from the volume of cancer cells to be killed or volume of tumor to which the virus-like particles are being administered.

Useful dosages of the freeze dried plant virus-like particles can be determined by comparing their in vitro activity and the in vivo activity in animal models. Methods for extrapolation of effective dosages in mice, and other animals, to humans are known in the art. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the freeze dried virus-like particles can vary depending upon many different factors, including means of administration, target site, physiological state of the patient, whether the patient is human or an animal, other medications administered, and whether treatment is prophylactic or therapeutic.

An Example has been included to more clearly describe particular embodiments of the invention. However, there are a wide variety of other embodiments within the scope of the present invention, which should not be limited to the particular example provided herein.

Example

Freeze Drying to Produce Efficacious CPMV Virus-Like Particles

We developed a streamlined method to produce eCPMV from native CPMV with a simple experimental setup and low demands for equipment and materials. A simple freeze-drying procedure ejected the RNA from the capsid and RNAse treatment was able to degrade the remaining nucleic acids, to produce lyo-eCPMV. A series of characterizations methods were carried out to show that the empty capsids maintained an intact capsid conformation. Furthermore, in situ injection of lyo-eCPMV was observed to have similar efficacy in tumor suppression as bacterially derived eCPMV. In sum, a straightforward method for the rapid production of eCPMV from native infectious CPMV is described herein.

Material and Methods

Ultrapure water (Milli-Q, Bedford, Mass.) was used for all experiments. Bovine serum albumins (BSA), monosodium phosphate anhydrate, disodium phosphate heptahydrate, sodium chloride, tris base for molecular biology, acetate acid, PEG 8000, RNase A and SimplyBlue™ SafeStain were purchased from Fisher Scientific. Bradford reagent was purchased from VWR Life Science. Agarose I, EDTA tetrasodium salt anhydrous and ethidium bromide were purchased from Amresco. Sucrose was purchased from Acros Organics.

Instrumentation

A VirTis Advantage EL-85 freeze dryer (SP Scientific, Warminster, Pa., USA) was used for lyophilization. Wyatt Möbiuζ® was used to perform DLS. Samples were analyzed at 25° C. in plastic disposable cuvettes with a path length of 10 mm. Fast protein liquid chromatography (FPLC) was performed using a AKTA-FPLC 900 chromatography system equipped with a Sephacryl 1000 SF 10/300 size exclusion column. The mobile phase used is 50 mM phosphate buffer, with 150 mM NaCl (pH 7.4) at a flow rate of 0.4 mL/min. Samples were injected at a concentration of 0.7 mg/mL. Native gel electrophoresis was performed using 1.2% agarose gels in 1×Tris acetate/EDTA (TAE) buffer. 1×TAE buffer was diluted from 50×TAE stock (2 mol tris-base, 0.9 mol acetate acid and 0.05 mol EDTA in Milli-Q water made up 1 liter 50×TAE stock). Running buffer is also 1×TAE buffer and 10 μg of sample was loaded.

CPMV Production and Purification

Black-eyed peas (*Vigna unguiculata*) were inoculated with 100 ng/μL CPMV in 0.1 M potassium phosphate buffer (pH 7.0) and propagated for 18-20 days using established procedures.

Lyo-eCPMV Production

CPMV was first filtered into deionized water using a 100K Amicon™ Ultra-4 centrifugal filter at 6,000 rpm (Eppendorf 5810 centrifuge) at least 6 times in order to remove salts and low molecular weight impurities from the product. The filtered CPMV stock was then adjusted to 1 mg/mL with deionized water and slowly frozen at −20° C. in a laboratory freezer for at least 4 days. The tray freeze dryer was used with a shelf temperature of 25° C. and an ultimate chamber pressure of 5 μbar. The final lyophilized particles exhibited a slightly yellow flocculent appearance.

Lyophilized particles were resuspended in 1 mL 0.1 M potassium phosphate buffer (pH 7.0) overnight. Resuspended particles were more turbid compared to the original CPMV suspension, indicating incomplete suspension of the original material. Centrifugation (Eppendorf 5424) was performed at 10,000 rpm for 5 minutes to precipitate the turbid material. The supernatant was collected and adjusted to ~1 mg/mL as determined by the Bradford assay. RNase A was then added to the resuspended lyo-CPMV at a concentration of 50 μg/mL. The samples were vortexed and incubated at room temperature for 15 min with gentle mixing by vortex at the level of 1.5. Following RNase treatment, 100K Amicon™ Ultra-4 centrifugal filters were used to remove RNAse A and degraded RNA (6,000 rpm in an Eppendorf 5810R, 0.1M KP, pH 7). Filtration was performed at least 6 times to completely remove degraded RNA fragments. Finally, the recovered particles were centrifuged at 10,000 rpm (Eppendorf 5424) for 5 min to remove any particulate aggregates.

Cryo Specimen Preparation and Image Collection

Three microliter aliquots of lyophilized, RNase A treated, and filtered CPMV (lyo-eCPMV) at 0.5 mg/mL were applied onto 300-mesh copper grids (Quantifoil R2/2) that were glow discharged for 20 sec at 20 mA. Excess solution was blotted for 1 sec with filter paper and the grids were immediately plunged into liquid ethane using a ThermoFisher/FEI Vitrobot. Cryo-EM data was collected on a JEOL 2200 FS microscope (FEG, in-column energy filter) operated at 200 kV. Images were recorded on a Direct Electron DE 20 detector at a magnification of 60,000× corresponding to a pixel value of 1.12 Å. Each micrograph was generated by averaging 32 individual dose fractionated frames collected at a rate of 20 frames/s for 1.6 s with an accumulated total dose of 63.3 electrons/pixel. The frames were motion corrected and summed into a single micrograph and processed. The micrographs were collected with underfocus values in the range of 1.6-3.5 μm.

Image Processing and 3D Reconstruction

Particle selection was performed using the EMAN2 software suite. A set of 16,628 particle images was selected from 181 cryo-electron micrographs. The defocus, and astigmatism values for each of the micrographs were estimated using CTFFIND 4.1. The RELION 2.1 software suite was used for further image processing. After the RELION 2D classification step, particle images in 40 out of 82 2D classes were selected for further processing (14,059 particle images selected). The cryo-EM structure of naturally empty eCPMV at 4.25 Å resolution was obtained from the Electron Microscopy Data Bank (EMD-3562) and was used as a reference map during 3D classification. The CPMV reference map was rotated to the I1 symmetry orientation and low-pass filtered to 10 Å resolution. After the RELION 3D classification step, particle images in 1 of 10 3D classes were selected for independent refinement with RELION 3D auto-refine. This class contains 8,135 particle images (58% of the total dataset) and refined to 17 Å resolution (at the Fourier Shell Correlation 0.143 threshold). Images were created with UCSF Chimera.

Cell Cultures

B16F10 cells (ATCC) were cultured in Dulbecco's modified Eagle's media (DMEM, Life Technologies) at 37° C. in a 5% $CO_2$ humidified atmosphere, supplemented with 10% (v/v) fetal bovine serum (FBS, Atlanta Biologicals) and 1% (v/v) penicillin-streptomycin (Life Technologies).

Immunization of Mice

All experiments were conducted in accordance with Case Western Reserve University's IACUC. $1.25 \times 10^5$ B16F10 cells/30 μL PBS were introduced intradermally into the right flank of C57BL/6J male (Jackson Laboratory). Animals were observed closely, and tumor size was measured with digital calipers. Tumor volumes were calculated as $V=0.5 (a \times b^2)$; where a is length and b is width of the tumor. Once tumor size reached 4-5 mm in the largest diameter, mice were randomized to the experimental groups: PBS and lyo-eCPMV (n=4). 100 μg of lyo-eCPMV and sterile PBS were injected into tumors in a volume of 30 μL every 4 days for total 3 treatments. Animals were sacrificed when tumors reached a volume $>1500$ mm$^3$.

Results

Results and Discussion

Lyo-eCPMV Production and Characterization

Figure 1:
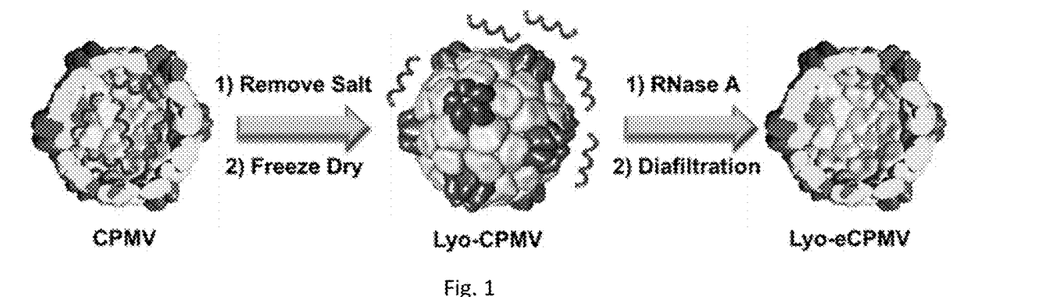
FIG. 1 illustrates a schematic diagram of the RNA removal from CPMV. Wildtype CPMV were freeze dried, which resulted in intact lyo-CPMV. RNase A was used to remove genomic RNA and generate lyo-eCPMV.

This method was found empirically and serendipitously when we tried to lyophilize CPMV particles for storage and device manufacture. Removal of RNA from the capsid begins with a slow freeze of a CPMV aqueous solution at −20° C. Temperature, time and concentration are factors during the freezing step prior to lyophilization. Typical freezing procedures using liquid $N_2$ were unable to eject the RNA, thus a slow freeze in a laboratory freezer (4 days), followed by lyophilization, resulted in ideal capsid uniformity and complete removal of RNA. Furthermore, concentration during freezing is a critical factor in obtaining sufficient yield. At high concentrations (>10 mg/mL) particles aggregate and significant fractions are unable to resuspend following lyophilization, however dilute solutions of ~1 mg/mL lessen particle aggregation and maintain high yields. Following freezing, a four-day negative pressure lyophilization was the shortest time required in order to achieve complete dehydration and RNA ejection based on our observations. The resulting dry powder was a mixture of RNA, intact RNA-free particle, and a small amount of protein aggregates; the resulting mixture of components is referred to as lyo-CPMV. Lyo-CPMV was resuspended into buffered solution and aggregates were removed by centrifugation and decanting. The last step in the lyo-eCPMV preparation is removal of genomic RNA. This was accomplished using RNase A, an extremely common endonuclease, to cleave the RNA into small fragments, which were easily removed using diafiltration with 100 kDa molecular weight cut-off centrifugal filters. Lyo-eCPMV was recovered at a yield of 0.8 g of particles/1 kg infected leaf tissue, which was competitive with the yield of eCPMV as prepared by agroinfiltration (see FIG. 1).

Characterization of RNA Content of Lyo-eCPMV and Particle Purity

Next we sought to determine particle integrity as well as residual RNA remaining in the CPMV VLPs. Agarose gel electrophoresis was performed to study particle integrity as well as the presence of residual genomic RNA following lyophilization (FIG. 2A). The placement of the bands is determined by the absolute mobility of the nanoparticles which is dependent on the presence of RNA within the capsid. Native CPMV showed two bands in ethidium bromide (EtBr) stained agarose gels as expected from two different electrophoretic forms of the virus (FIG. 2A). By contrast, lyo-CPMV only showed a single strong band with high electrophoretic mobility when staining for nucleic acids. The broad band likely corresponds to RNA-1 and RNA-2 from CPMV, which are not separated due to gel resolution and over-loading once RNA is released. This band did not colocalize with any protein stain, which suggested that RNA was ejected during the lyophilization process. Finally, lyo-eCPMV showed no EtBr stained band which suggested no detectable level of nucleic acids were present. Coomassie was then used to stain the gel in order to visualize the protein component of CPMV. Wild-type CPMV showed two bands as expected, however, lyo-CPMV and lyo-eCPMV showed a single band that coalesced between the two bands of wild-type CPMV, which is consistent with previous reports of RNA-free CPMV. Taken together, agarose gel electrophoresis gave strong indication that RNA was ejected to form a nucleic-acid free VLP.

Further evidence of RNA removal can be found in UV-Vis spectroscopy (FIG. 2B); the encapsulated nucleic acids have a dominant absorbance peak at 260 nm, while absorbance at 280 nm is reflective of the protein capsid with a lesser contribution from the nucleic acids. The ratio between these two absorbance intensities is indicative of RNA presence in the final material. Wild-type CPMV had a $A_{260}/A_{280}$ ratio of 1.573 which correlated with the literature value of 1.57, and suggested RNA encapsulation, as would be expected. The $A_{260}/A_{280}$ ratio of lyo-CPMV increased to 2.090 which is a result of RNA unfolding and ejection from the capsid. The unusually high ratio is likely further skewed due to insoluble protein precipitate. Finally, the absorbance ratio of lyo-eCPMV dramatically dropped to 0.804, indicating that nearly all RNA was removed. This value is slightly higher than the literature value of eCPMV at 0.69, which likely indicates the presence of trace nucleic acids either in the supernatant or encapsulated within lyo-eCPMV.

Agarose gels only give comparative sizes based on the band position of known standards. Dynamic light scattering (DLS) and fast protein liquid chromatography (FPLC) were carried out to further characterize lyo-CPMV and lyo-eCPMV size and purity, respectively (FIG. 3). DLS measurements show that the lyophilization and "post-processing" method have minimal impact on particle size and aggregation (FIG. 3A). The DLS data indicate no obvious aggregates or collapsed protein subunits for wild-type CPMV, with a hydrodynamic radius of 16.4 nm. The hydrodynamic radius of lyo-CPMV is approximately the same ($R_h$=14.5 nm), indicating that minimal aggregation occurred during the freeze-drying step. The hydrodynamic radius of lyo-eCPMV (14.9 nm) also showed little difference compared to wild-type CPMV. FPLC was used to determine particle purity (FIG. 3B). Wild-type CPMV displays a single Gaussian peak centered at ~19 mL elution volume Sephacryl 1000 SF 10/300 size exclusion column. In contrast, lyo-CPMV exhibited a single peak centered at a slightly higher elution volume (~21 mL), which is no longer symmetric. This change can be attributed to released RNA remaining in the sample, since the genomic RNA is of reduced hydrodynamic volume relative to the capsid. Further confirmation of this is evidenced by the high $A_{260}/A_{280}$ ratio (>2.0), indicating a high concentration of nucleic acid. Once RNA was removed by nuclease treatment to form lyo-eCPMV, the $A_{260}/A_{280}$ ratio was reversed and a stark decrease in total absorbance was seen indicating the absence of nucleic acids. Furthermore, the elution volume returned to ~19 mL and regained symmetry indicating intact viral capsids, with a minimal shoulder at lower elution volumes perhaps indicating a small population of aggregated species.

Cryo-EM Examination of Lyo-eCPMV

Figure 4A:
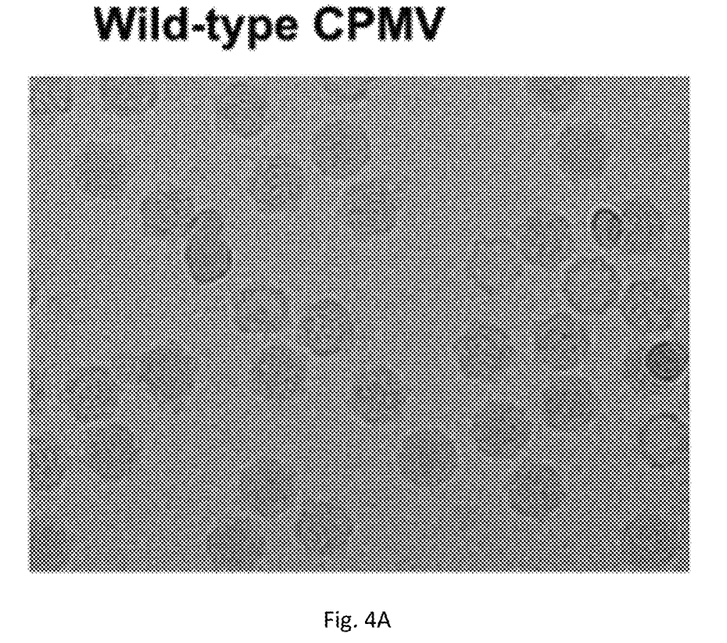
Figure 4B:
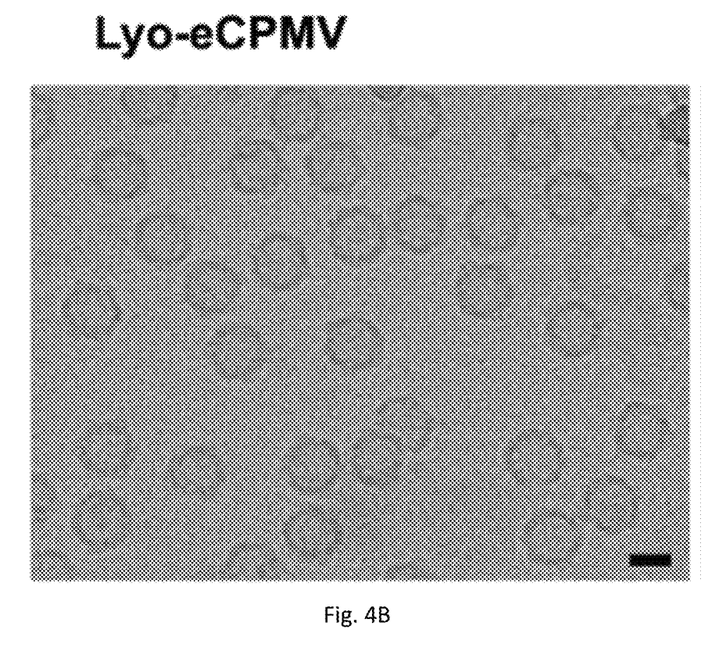
Figure 5A:
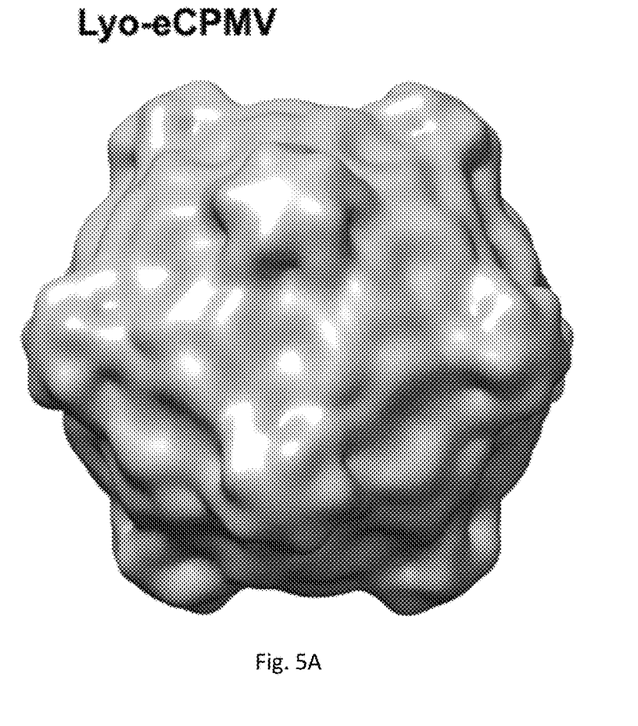
Figure 5B:
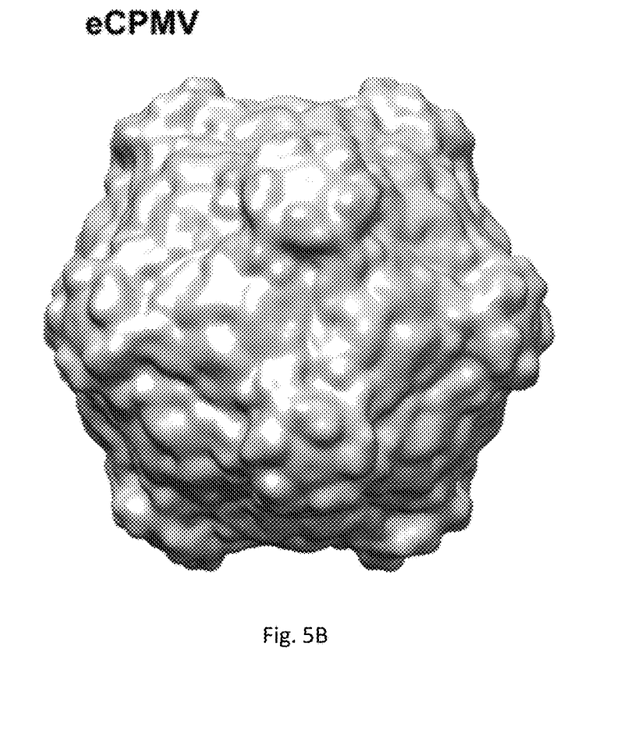
Figure 6A:
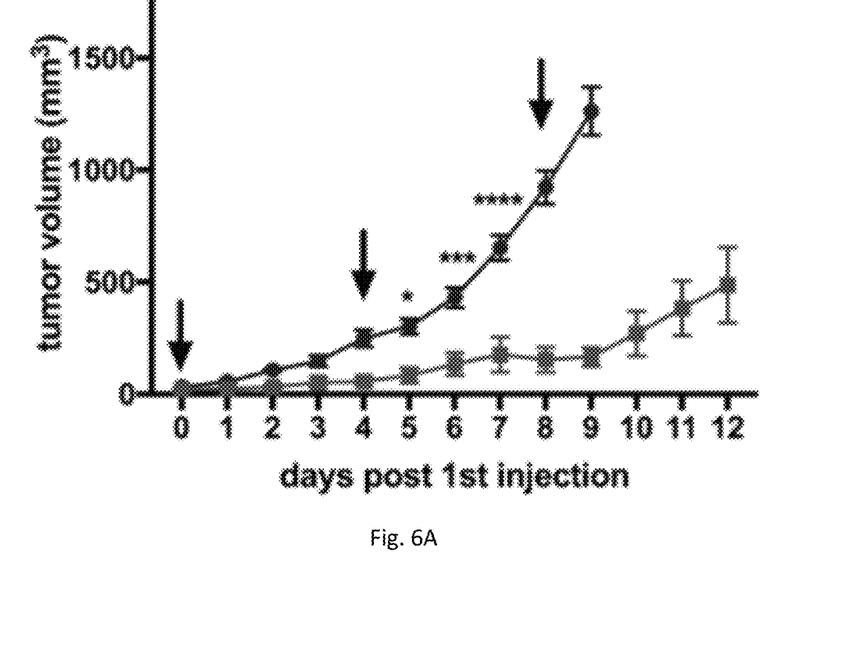
Figure 6B:
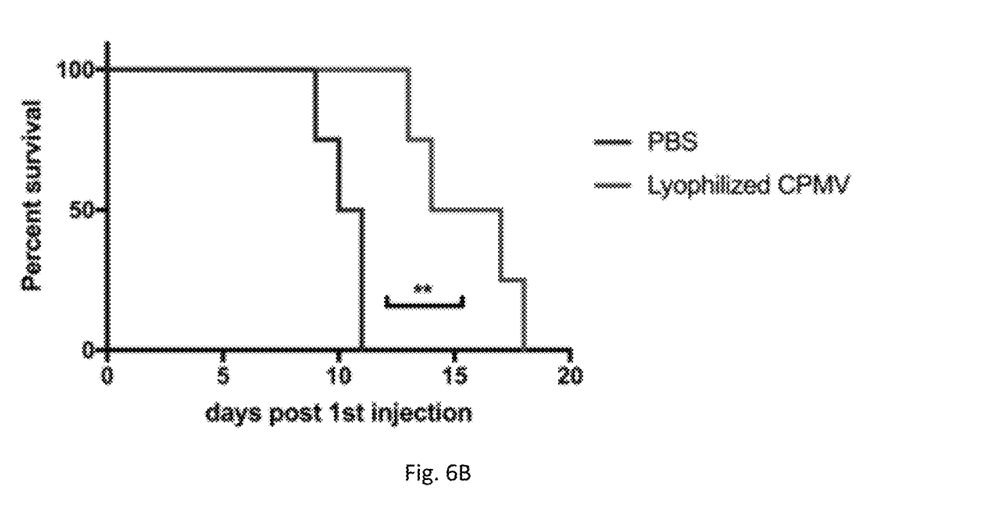

The structural integrity of lyo-eCPMV particles was examined by cryo-electron microscopy (cryo-EM). As expected cryo-electron micrographs of wild-type CPMV particles show dark interiors, indicative of the presence of encapsulated RNA (FIG. 4A). In contrast, lyo-eCPMV particles have lighter interiors and appear to be empty (FIG. 4B). The cryo-electron micrographs also suggest that the icosahedral capsids of lyo-eCPMV particles are largely well-formed and structurally intact. Single particle reconstruction was performed on a dataset of ~16,600 lyo-eCPMV particle images collected on a 200 kV cryo-electron microscope with an energy filter and a DE20 direct electron detector. Classification with RELION helped to select a relatively homogeneous subset of ~8,000 particle images. Refinement of this subset produced a 17 Å resolution structure (FIG. 5A). The lyo-eCPMV cryo-EM structure reproduces many of the structural features observed in a cryo-EM structure of naturally occurring eCPMV filtered to the same resolution (FIG. 5B).

The cryo-EM reconstruction of lyo-eCPMV shows slight perturbances in the capsid structure. Few reports have investigated the effects of lyophilization on viral capsids, however, potential reasons for particle disruption can be inferred from literature regarding protein freeze drying. During the freezing and drying step, the solution concentration drastically increases, this can lead to changes in pH and osmolyte concentration. During this process, acidic groups are typically protonated, disrupting salt-bridges and leading to destabilization of biological structures. It is likely that this effect caused disruption between the genomic RNA and coat protein. Furthermore, as the osmolyte concentration increases, so too does the internal pressure within the viral capsid, potentially leading to swelling of the particle. It is likely these two effects both destabilize RNA binding and lead to ejection of the RNA from the capsid. Once rehydrated, the disrupted lyo-eCPMV capsid appears to bounce back into a structure that resembles that of naturally occurring eCPMV.

In Situ Vaccination with Lyo-eCPMV

The most critical part of our method to make lyo-eCPMV is its ability to remain as a potent in situ cancer vaccine. Given the structural similarity of lyo-eCPMV to naturally occurring eCPMV as observed by cryo-EM single particle reconstruction, we were optimistic that lyo-eCPMV would retain similar anti-tumor properties in the treatment of melanoma. To confirm efficacy, we used the same murine melanoma model with which we had seen success with eCPMV. C57BL/6J male mice were inoculated with B16F10 murine melanoma cells subcutaneously. Treatment was started once the tumor size reached 4-5 mm in the largest diameter. Tumors were injected directly with 100 μg lyo-eCPMV at 0, 4, and 8 days. By day 4, significant differences were seen in tumor volume, and by day 8, the tumor volume of control mice was nearly an order of magnitude greater than lyo-eCPMV treated animals. Mice treated with lyo-eCPMV particles had significantly delayed tumor progression and survival was extended by ~100% (FIG. 6). This result was similar to eCPMV treatment in previous studies, which suggested lyo-eCPMV has comparable immunostimulatory capabilities as naturally occurring eCPMV. In sum, our results represent a novel way to prepare genome-free virus-like particles from infectious virions while maintaining efficacy.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of producing plant virus-like particles, the method comprising:

freezing drying an aqueous solution of plant virus particles to produce substantially RNA-free plant virus-like particles, wherein the plant virus particles have an icosahedral structure.

2. The method of claim 1, the aqueous solution of plant virus particles includes plant virus particles at a concentration of less than about 10 mg/ml.

3. The method of claim 1, wherein the freeze drying includes freezing an aqueous solution of the plant virus particles at a temperature and for an amount of time that allows the plant virus particles to eject encapsulated genomic RNA while maintaining an intact capsid conformation.

4. The method of claim 3, wherein the freeze drying includes heating the frozen aqueous solution at a temperature above freezing and at a pressure less than about 100 millibar to sublimate frozen water.

5. The method of claim 1, further comprising contacting the freeze dried plant virus particles with RNase to degrade nucleic acid.

6. The method of claim 1, wherein the plant virus particles comprise picornavirus particles.

7. The method of claim 6, wherein the plant picornavirus particles are of the *Comovirus* genus.

8. The method of claim 6, wherein the picornavirus comprising cowpea mosaic virus (CPMV).

9. A method of producing empty plant virus-like particles, the method comprising:

freezing an aqueous solution of plant virus particles at a temperature and for an amount of time that allows the plant virus particles to eject the encapsulated genomic RNA while maintaining an intact capsid conformation, wherein the plant virus particles have an icosahedral structure; and sublimating the frozen aqueous solution of plant virus particles to remove water and RNA in the plant virus capsid.

10. The method of claim 9, the aqueous solution of plant virus particles includes plant virus particles at a concentration of less than about 10 mg/ml.

11. The method of claim 9, wherein the aqueous solution of the plant virus particles is frozen at a temperature of about −5° C. to about −40° C.

12. The method of claim 9, wherein the step of sublimating the frozen aqueous solution includes heating the frozen aqueous solution at a temperature above freezing and at a pressure less than about 100 millibar.

13. The method of claim 9, further comprising contacting the freeze dried plant virus particles with RNase to degrade nucleic acid.

14. The method of claim 9, wherein the plant virus particles comprise picornavirus particles.

15. The method of claim 14, wherein the plant picornavirus particles are of the *Comovirus* genus.

16. The method of claim 14, the picornavirus comprising cowpea mosaic virus (CPMV).

17. A composition comprising a plurality of freeze dried, endoribonuclease treated plant virus-like particles prepared by the method of claim 1; wherein the plant virus-like particles have an icosahedral structure.

18. The composition of claim 17, wherein during freeze drying an aqueous solution of icosahedral plant virus particles is frozen at a temperature and for an amount of time that allows the virus to eject encapsulated genomic RNA while maintaining an intact capsid conformation.

19. The composition of claim 17, wherein freeze drying includes heating a frozen aqueous solution of icosahedral plant virus particles at a temperature above freezing and at a pressure less than about 100 millibar.

20. The composition of claim 17, wherein the endoribonuclease comprises RNaseA.

21. The composition of claim 17, wherein the plant virus-like particles comprise cowpea mosaic virus-like particles.

\* \* \* \* \*